United States Patent
Li et al.

(10) Patent No.: US 7,544,687 B2
(45) Date of Patent: Jun. 9, 2009

(54) SUBSTITUTED α-PIPERAZINYL PHENYLPROPIONIC ACID DERIVATIVES AS HPPAR α AND/OR HPPAR γ AGONISTS

(75) Inventors: Song Li, Beijing (CN); Xinbo Zhou, Beijing (CN); Lili Wang, Beijing (CN); Cheng Xu, Beijing (CN); Chengmai Ruan, Beijing (CN); Cuifang Lin, Beijing (CN); Junhai Xiao, Beijing (CN); Zhibing Zheng, Beijing (CN); Hongying Liu, Beijing (CN); Yunde Xie, Beijing (CN); Wu Zhong, Beijing (CN); Hao Cui, Beijing (CN)

(73) Assignee: Beijing Molecule Science and Technology Co., Ltd, Beijing (CN)

( * ) Notice: Subject to any disclaimer, the term of this patent is extended or adjusted under 35 U.S.C. 154(b) by 115 days.

(21) Appl. No.: 11/569,575

(22) PCT Filed: Feb. 2, 2005

(86) PCT No.: PCT/CN2005/000148
§ 371 (c)(1),
(2), (4) Date: Dec. 15, 2006

(87) PCT Pub. No.: WO2005/116018
PCT Pub. Date: Dec. 8, 2005

(65) Prior Publication Data
US 2007/0259883 A1   Nov. 8, 2007

(30) Foreign Application Priority Data
May 24, 2004   (CN) .......................... 2004 1 0042573

(51) Int. Cl.
A61K 31/496 (2006.01)
C07D 263/32 (2006.01)
(52) U.S. Cl. .................................. 514/254.02; 544/369
(58) Field of Classification Search ...................... None
See application file for complete search history.

(56) References Cited

U.S. PATENT DOCUMENTS 6,194,446 B1  2/2001  Dominianni et al.
6,506,781 B1  1/2003  Cobb et al.

FOREIGN PATENT DOCUMENTS

| CN | 1321152 | 11/2001 |
|---|---|---|
| JP | 2000344748 | 12/2000 |
| WO | 03059895 | 7/2003 |
| WO | 2004067495 | 8/2004 |
| WO | WO03066574 | 12/2006 |

OTHER PUBLICATIONS

Reynolds et al. Tetrahedron, vol. 57, p. 7765-7770 (2001).*
Vippagunta et al. Advanced Drug Delivery Reviews, vol. 48, p. 3-26 (2001).*
Kevin G. Liu et al., Synthesis and Biological Activity of L-Tyrosine-Based PPARγ Agonists With Reduced Molecular Weight,(2001), pp. 3111-3113, Bioorganic & Medicinal Chemistry Letters 11,Elsevier Science Ltd.
Yi Xiang and Guo Zong-Ru, Study on 3D-QSAR of PPARγ Agonists With Thiazolidinedione and Arylketo-Acid Moieties,(2001),36 (4) pp. 262-268, Acta Pharmaceutica Sinica China.
Cai Zhe-Feng and Guo Zong-Ru, Peroxisome Poliferator-Activated Receptors and There Modulators, (2004) 39 (2) pp. 158-160, Acta Pharmaceutica Sinica China.
Cheng Feng, et al., Research Progress in PPARγ Agonists, (2003), vol. 13 No. 2 p. 110, Chinese Journal of Medicinal Chemistry.

* cited by examiner

*Primary Examiner*—Emily Bernhardt
(74) *Attorney, Agent, or Firm*—Lucas & Mercanti, LLP

(57) ABSTRACT

The present invention relates to a compound of formula I, racemates, optically active isomers, or pharmaceutically acceptable salts or solvates thereof, and a pharmaceutical composition comprising the compound, the various radicals in the formula I are the same as defined in the claims. The present invention also relates to a process for preparing the compound of formula I and use of said compound in the preparation of a medicament for the treatment of hyperglycemia, dyslipidemia, type II diabetes mellitus including associated diabetic dyslipidemia.

9 Claims, No Drawings

SUBSTITUTED α-PIPERAZINYL PHENYLPROPIONIC ACID DERIVATIVES AS HPPAR α AND/OR HPPAR γ AGONISTS

FIELD OF THE INVETION

The present invention relates to substituted α-piperazinyl phenylpropionic acid derivatives or pharmaceutically acceptable salts or solvates thereof, processes for preparing them, pharmaceutical composition comprising them, and their use, as agonists of peroxisome proliferator-activated receptor (abbreviated as PPAR), in particular as double agonists of PPARγ and PPARα, for the prevention and/or treatment of metabolic diseases such as diabetes and hyperlipidemia.

BACKGROUND OF THE INVENTION

Peroxisome Proliferator Activated Receptors (PPAR's), alike glucocorticoid receptors, tretinoin receptors and thyroid receptors, are ligand-dependent transcription factors pertaining to intranuclear receptor superfamily. PPAR can be subdivided into three subtypes: PPARα, PPARγ and PPARδ (also known as PPARβ and NUC1), which are encoded by different genes. Moreover, PPARγ also have two isoforms, i.e., PPARγ$_1$ and PPARγ$_2$. These two proteins differ in their 30 amino acids at NH$_2$-terminal, which are resulted from the alternative use of promoter and the differential splicing of nRNA (Vidal-Puig, J. Clin. Invest., 97:2553-2561, 1996).

PPARα is mainly expressed in the tissues, such as brown adipose tissue and liver, having high catabolic capacity for lipids, followed by kidney, heart and skeletal muscle (Endocnnology, 1995, 137, 354). It can positively or negatively control the expression of genes related to the metabolism and the intracellular transport of fatty acid (e.g. acyl CoA synthetase, fatty acid-binding protein and lipoprotein lipase) and of apolipoprotein (AI, AII, CIII) genes related to the metabolisms of cholesterol and neutral lipids. PPARγ is found at high levels in adipose tissue and at lower levels in skeletal muscle, liver, colon, retina and immune system. Recently, it was found at high levels in macrophages, including atherosclerorotic foam cell. Of which, PPARγ$_2$ was specifically expressed predominantly in adipose tissue. In contrast, PPARγ$_1$ had a broad tissue expression, and was expressed at the highest levels in kidney, intestines and heart. PPARγ serves as a key regulator for adipocyte differentiation and expression of insulin-sensitive genes (J. Lipid Res., 1996, 37, 907).

PPARδ is expressed ubiquitously in the tissues of organisms with nerve cells as the center. At present, the physiological significance of PPARδ is still unclear.

Thiazolidinedione drugs, for example troglitazone and rosiglitazone, were clinically shown to be capable of enhancing insulin-action and reducing serum glucose in patients with Type 2 diabetes. It has been reported that thiazolidinediones are potent and selective activators of PPARγ and bind directly to the PPARγ receptor (J. M. Lehmann, et. al., J. Blol. Chem. 2953-12956, 270 (1995)).

Fibrates were widely used as a class of drugs for treating hyperlipidemia, which might lower serum triglycerides by 20-50%, lower LDLc by 10-15%, and increase HDLc by 10-15%. Experimental evidence indicated that the effects of fibrates on serum lipids were mediated through activation of PPARα. See, for example, B. Staels, et al., Curr. Pharm. Des., 7-14, 3(1), (1997). Activation of PPARα resulted in transcription of enzymes that increased fatty acid catabolism and decreased fatty acid re-synthesis in the liver (leading to decrease of triglyceride synthesis and VLDL production/secretion). In addition, activation of PPARα decreased production of apoC-III. The reduction in production of apoC-III (an inhibitor of LPL activity) increased clearance of VLDL (J. Auwerx, et al., Atherosclerosis, J59-S37, 124 (Suppl), (1996)).

The results of the existing technology showed that a dual agonist of PPARα and PPARγ had additional advantage for reducing other abnormity, in particular increased triglyceride, concomitant with diabetes. See, for example, U.S. Pat. No. 5,478,852, WO 98/05331.

CONTENTS OF THE INVENTION

The object of the present invention is to search and develop a small molecular compound as agonist of PPARα and PPARγ, which compound is effective for treating hPPARα and/or hPPARγ mediated diseases, risk factors or disorders. After research, the present inventor discovers that the compound having the following general formula I is an agonist of PPARα and PPARγ, and therefore is effective for preventing and/or treating diseases or symptoms, e.g., diabetes or hyperglycemia, associated with PPARα and PPARγ. The inventor further discovers that the compound of formula I also has an excellent lipid-reducing effect.

Therefore, in one aspect, the present invention relates to compounds of the general formula I, racemates, optically active isomers, or pharmaceutically acceptable salts or solvates thereof,

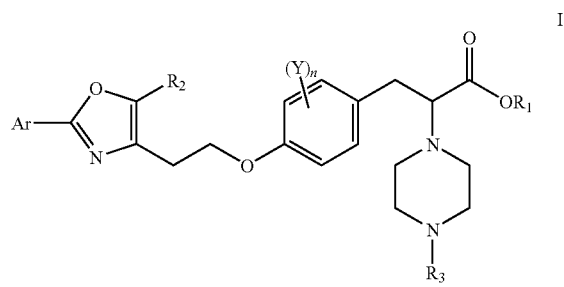

wherein:
R$_1$ and R$_2$ are independently hydrogen, or C$_{1-4}$ straight or branched alkyl;
R$_3$ is Ar$_1$ or —SO$_2$Ar$_1$;
Ar and Ar$_1$ are independently selected from mono-, di-, or tricyclic aromatic carbocyclic ring or heterocyclic ring containing 1 to 4 heteroatoms selected from a group consisting of O, S and N; wherein each single ring is 5- or 6-membered ring; and said ring is unsubstituted or substituted with 1 to 5 of the following groups: halogens, nitro, hydroxy, hydroxymethyl, trifluoromethyl, trifluoromethoxy, C$_1$-C$_6$ straight or branched alkyl, C$_2$-C$_6$ straight or branched alkenyl, C$_1$-C$_4$ alkoxy, C$_2$-C$_4$ alkenoxy, phenoxy, benzyloxy, carboxyl or amino;

In another aspect, the present invention relates to a pharmaceutical composition comprising at least one compound of formula I, or racemate, optically active isomer or pharmaceutically acceptable salt or solvate thereof, and one or more pharmaceutically acceptable carriers or excipients.

In another aspect, the present invention provides a process for preparing the compounds of Formula I or pharmaceutically acceptable salts or solvates thereof.

In still another aspect, the present invention relates to the preparation of intermediate compounds used for preparing the compounds of Formula I or pharmaceutically acceptable salts or solvates thereof.

In still another aspect, the present invention relates to use of the compound of formula I in the manufacture of a medicament for the treatment or prevention of hPPARα and/or hPPARγ mediated diseases, risk factors or conditions.

The hPPARγ and/or hPPARα mediated diseases, risk factors, or conditions include hyperglycemia, dyslipidemia, type II diabetes mellitus including associated diabetic dyslipidemia, type I diabetes, hypertriglyceridemia, syndrome X, insulin resistance, heart failure, hyperlipidemia, hypercholesteremia, hypertension, cardiovascular disease including atherosclerosis, regulation of appetite and food intake in subjects suffering from conditions such as obesity, anorexia, anorexia bulimia, and anorexia nervosa.

Specifically, in one embodiment, the present invention relates to compounds of the general formula I, racemates, optically active isomers, or pharmaceutically acceptable salts or solvates thereof,

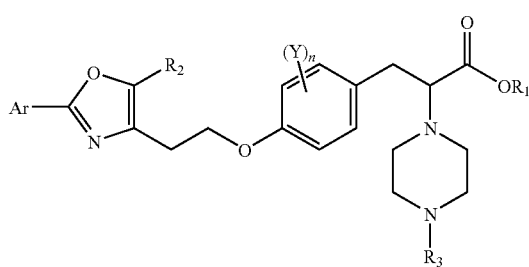

I wherein:
$R_1$ and $R_2$ are independently hydrogen, or $C_{1-4}$ straight or branched alkyl;
$R_3$ is $Ar_1$ or —$SO_2Ar_1$;
Ar and $Ar_1$ are independently selected from mono-, di-, or tricyclic aromatic carbocyclic ring and heterocyclic ring containing 1 to 4 heteroatoms selected from a group consisting of O, S and N, wherein each single ring is a 5- or 6-membered ring, and said ring is unsubstituted or substituted with 1 to 4 of the following groups: halogen, nitro, hydroxy, hydroxymethyl, trifluoromethyl, trifluoromethoxy, $C_1$-$C_6$ straight or branched alkyl, $C_2$-$C_6$ straight or branched alkenyl, $C_1$-$C_4$ alkoxy, $C_2$-$C_4$ alkenoxy, phenoxy, benzyloxy, carboxyl or amino;
Y is hydrogen or halogen;
n is an integer from 1 to 4.

In one preferred embodiment, the compounds of formula I are S-configuration isomers of formula II, or pharmaceutically acceptable salts or solvates thereof,

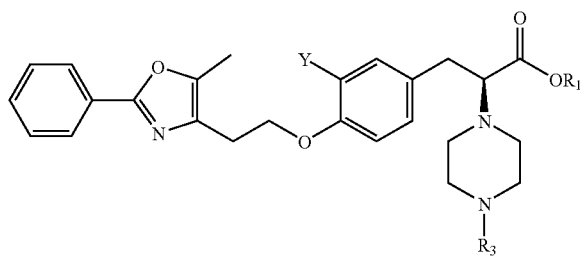

II wherein:

carbon atom bonded to $COOR_1$ is in the S configuration;
$R_1$ is hydrogen or methyl;
$R_3$ is $Ar_1$ or —$SO_2Ar_1$;
$Ar_1$ is phenyl ring which is unsubstituted or optionally substituted with 1 to 5 of the following groups: halogen, nitro, hydroxy, hydroxymethyl, trifluoromethyl, trifluoromethoxy, $C_1$-$C_6$ straight or branched alkyl, $C_2$-$C_6$ straight or branched alkenyl, $C_1$-$C_4$ alkoxy, $C_2$-$C_4$ alkenoxy, phenoxy, benzyloxy, carboxyl or amino;
Y is hydrogen or bromo.

Preferred compounds of the present invention include:
(2S)-3-{4-[2-(5-methyl-2-phenyl-1,3-oxazol-4-yl)-ethoxy]-phenyl}-2-(4-m-tolyl-piperazin-1-yl)-propionic acid;

(2S)-2-[4-(4-nitro-benzenesulfonyl)-piperazin-1-yl]-3-{4-[2-(5-methyl-2-phenyl-1,3-oxazol-4-yl)-ethoxy]-phenyl}-propionic acid;

(2S)-2-[4-(2-fluoro-benzenesulfonyl)-piperazin-1-yl]-3-{4-[2-(5-methyl-2-phenyl-1,3-oxazol-4-yl)-ethoxy]-phenyl}-propionic acid;

(2S)-2-[4-(4-fluoro-benzenesulfonyl)-piperazin-1-yl]-3-{4-[2-(5-methyl-2-phenyl-1,3-oxazol-4-yl)-ethoxy]-phenyl}-propionic acid;

(2S)-2-(4-benzenesulfonyl-piperazin-1-yl)-3-{4-[2-(5-methyl-2-phenyl-1,3-oxazol-4-yl)-ethoxy]-phenyl}-propionic acid;

(2S)-2-[4-(2-nitro-benzenesulfonyl)-piperazin-1-yl]-3-{4-[2-(5-methyl-2-phenyl-1,3-oxazol-4-yl)-ethoxy]-phenyl}-propionic acid;

(2S)-2-[4-(m-chloro-phenyl)-piperazin-1-yl]-3-{4-[2-(5-methyl-2-phenyl-1,3-oxazol-4-yl)-ethoxy]-phenyl}-propionic acid;

(2S)-3-{4-[2-(5-methyl-2-phenyl-1,3-oxazol-4-yl)-ethoxy]-phenyl}-2-(4-phenyl-piperazin-1-yl)-propionic acid;

(2S)-3-{3-bromo-4-[2-(5-methyl-2-phenyl-1,3-oxazol-4-yl)-ethoxy]-phenyl}-2-(4-p-tolyl-piperazin-1-yl)-propionic acid; and (2S)-3-{3-bromo-4-[2-(5-methyl-2-phenyl-1,3-oxazol-4-yl)-ethoxy]-phenyl}-2-(4-phenylpiperazin-1-yl)-propanoic acid;

or pharmaceutically acceptable salts or solvates thereof.

The compounds of formula I, or pharmaceutically acceptable salts or solvates thereof may be synthesized through the following methods:

Method 1:
Reacting a compound of formula V

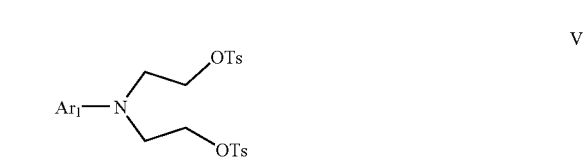

V wherein Ar₁ is the same as defined above for formula I, with a compound of formula III

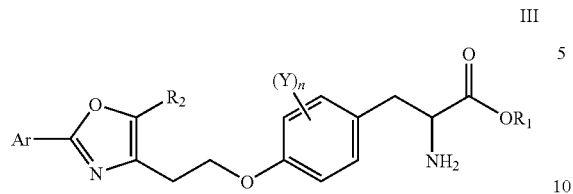

wherein Ar, $R_1$, $R_2$, Y and n are the same as defined above for formula I, to obtain the compound of formula I wherein $R_3$ represents $Ar_1$,

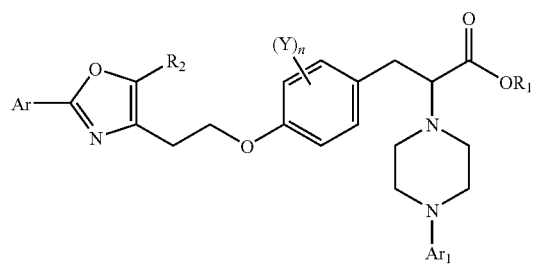

and $Ar_1$, Ar, $R_1$, $R_2$, Y and n are the same as defined above for formula I.

The compound of formula V used herein is commercially available, or is prepared by reacting a compound of formula IV:

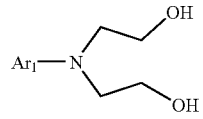

wherein Ar₁ is the same as defined above for formula I, with p-toluenesulfonyl chloride (see: Palmer, B. D., et al. Synth Commun 1987, 17, 601; GRAVATT, G. L., et al., J. Med. Chem. 1991, 34(5), 1552-1560).

Method 2:
1) Reacting the compound of formula III with N,N-bis-(2-bromoethyl)-amine hydrobromate to obtain a compound of formula VI

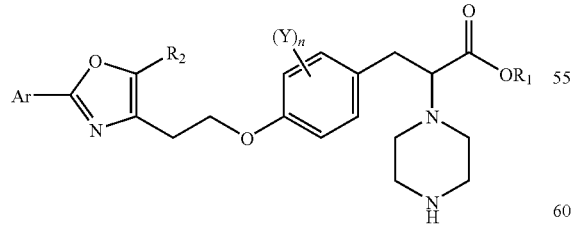

wherein Ar, $R_1$, $R_2$, Y and n are the same as defined above for formula I;
2) reacting the compound of formula VI with arylsulfonyl chloride ($Ar_1SO_2Cl$) to obtain the compound of formula I wherein $R_3$ represents $-SO_2Ar_1$

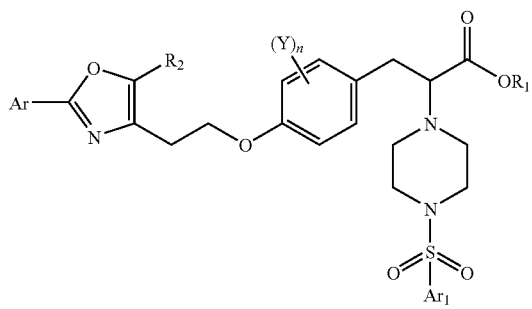

and $Ar_1$, Ar, $R_1$, $R_2$, Y and n are the same as defined above for formula I.

If desired, a compound of formula I can be converted to another compound of formula I in a different form. For example, a compound of formula I, wherein $R_1$ represents hydrogen, may be obtained by reacting, a compound of formula I wherein $R_1$ represents $C_1$-$C_4$ straight or branched alkyl, with an alkali metal hydroxide.

In a further aspect, the present invention relates to a method of preparing a compound of formula III, comprising:
1) subjecting an arylformamide, which is commercially available or prepared by a common method, and the compound of formula VII (wherein $R_4$ represents $C_1$-$C_4$ alkyl and $R_2$ is the same as defined above for formula I) to a ring closure reaction to thereby obtain the compound of formula VIII, wherein Ar and $R_2$ are the same as defined above for formula I, and $R_4$ represents $C_1$-$C_4$ alkyl; reducing the compound of formula VIII with lithium aluminum hydride (LiAlH₄) to obtain a compound of formula IX, wherein Ar and $R_2$ are the same as defined above for formula I; the compound of formula VII may be prepared by referring to Chem. Pharm. Bull. (1986), 34(7), 2840-51; and J. Med. Chem. (1992), 35(14), 2617-26;

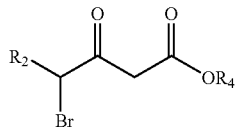

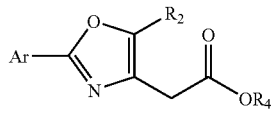

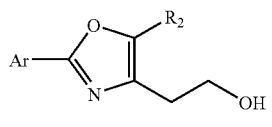

2) reacting a compound of formula X (wherein Y and n are the same as defined above for formula I, preferably Y is hydrogen or n is 1 and Y is Br in the ortho position of hydroxy group), with $R_1OH$ (wherein $R_1$ is the same as defined above for formula I, preferably $R_1$ is methyl) and thionyl chloride ($SOCl_2$), followed by reacting with di-tert-butyl dicarbonate ($BOC_2O$), to give a compound of formula XI (wherein $R_1$, Y and n are the same as defined above for formula I); the compound of formula X wherein n is 1 and Y is Br in the ortho position of hydroxy group may be prepared from the reaction of tyrosine with bromine;

3) reacting the compound of formula IX obtained in the step 1) with the compound of formula XI obtained in the step 2) to obtain a compound of formula XII,

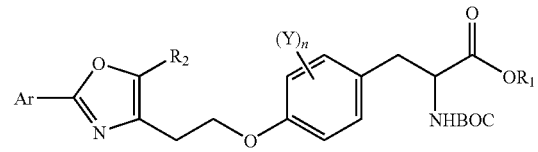

XII

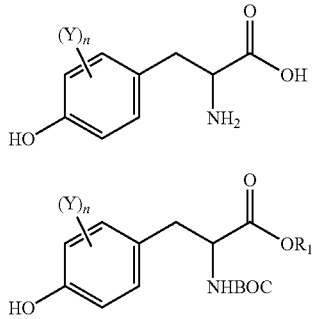

X

XI wherein Ar, $R_1$, $R_2$, Y and n are the same as defined above for formula I; and then deprotecting the compound of formula XII with trifluoroacetic acid to give the compound of formula II.

More concretely, the compounds of formula I can be synthesized through the following routes:

Scheme 1: synthesis of the compound of Formula III

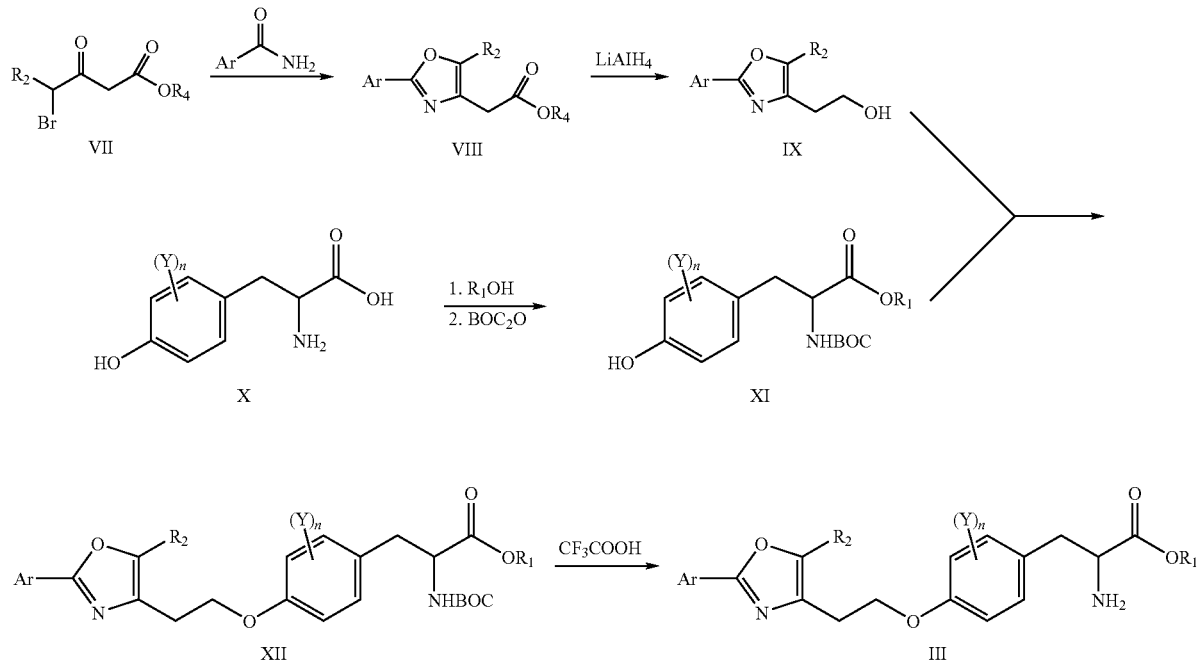

Step 1:

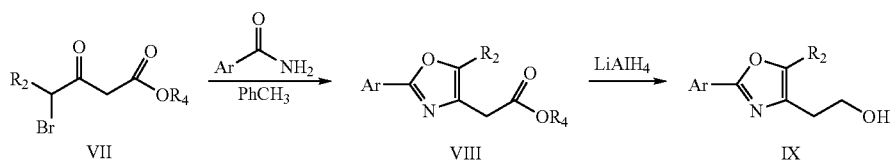

A compound of formula VII reacts with an arylformamide for 6-30 h under the condition of reflux in toluene, followed by concentration and purification with silica gel column chromatography (using n-hexane/EtOAc as an eluent), to obtain a compound of formula VIII as brown oil. The compound of formula VIII reacts with LiAlH$_4$ (purchased from Huanwei Fine Chemicals Co., Tianjin) in Et$_2$O at room temperature for 1-24 h, to which water, NaOH aqueous solution and MgSO$_4$ are carefully dropped in turn, followed by stirring for 0.1-1 h. The resulting solution is filtered, and then the filtrate is concentrated and purified by silica gel column chromatography (using n-hexane/EtOAc as an eluent) to obtain a white solid compound of formula IX, wherein R$_4$ is C$_1$-C$_4$ alkyl, and Ar, R$_2$ are the same as defined above for formula I.

Step 2:

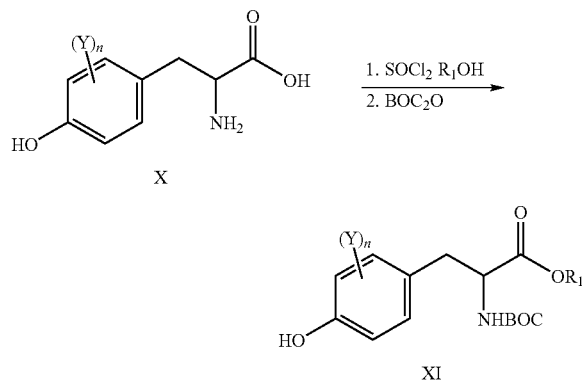

A compound of formula X (wherein Y and n are the same as defined above for formula I, preferably Y is hydrogen or n is 1 and Y is Br in the ortho position of hydroxy group) is refluxed for 1 to 10 h with R$_1$OH (wherein, R$_1$ is preferably CH$_3$) and SOCl$_2$, followed by concentration. The obtained residue reacts with BOC$_2$O for 1 to 8 h at room temperature in anhydrous CH$_3$CN under the catalysis of triethylamine, before concentration. The obtained product is dissolved with dichloromethane, washed with NaHSO$_4$ aqueous solution, saturated sodium carbonate aqueous solution and saturated brine in turn, and then dried with anhydrous magnesium sulfate, before concentration and recrystallization with ethyl ether to obtain a compound of formula XI wherein Y, R$_1$ and n are the same as defined above for formula I as a white solid. The compound of formula X wherein n is 1 and Y is Br in the ortho position of hydroxy group may be prepared from the reaction of tyrosine and bromine in glacial acetic acid at room temperature for 0.5 to 48 h.

Step 3:

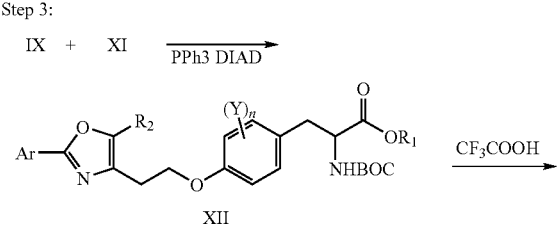

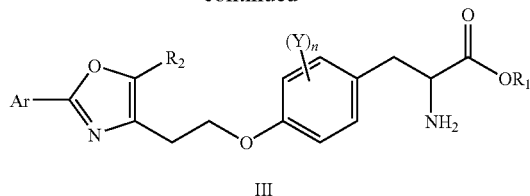

A compound of formula IX reacts with a compound of formula XI under the catalysis of triphenylphosphine (PPh$_3$) and diisopropyl azodiformate (DIAD) in anhydrous THF at room temperature for 1 to 30 h, followed by concentration and purification with silica gel column chromatography (using n-hexane/EtOAc as an eluent) to obtain a compound of formula XII (wherein Ar, R$_1$, R$_2$, Y and n are the same as defined above for formula I) as brown oil. The compound of formula XII is deprotected with trifluoroacetic acid in CH$_2$Cl$_2$ at room temperature for 1 to 10 h. The reaction mixture is neutralized with 0.5% NaOH aqueous solution, from which an organic layer is separated and dried, followed by concentration and purification with silica gel column chromatography (using n-hexane/EtOAc as an eluent) to give a compound of formula III (wherein Ar, R$_1$, R$_2$, Y and n are the same as defined above for formula I) as brown oil.

Scheme 2: Synthesis of the compound of formula I wherein R$_3$ is Ar$_1$

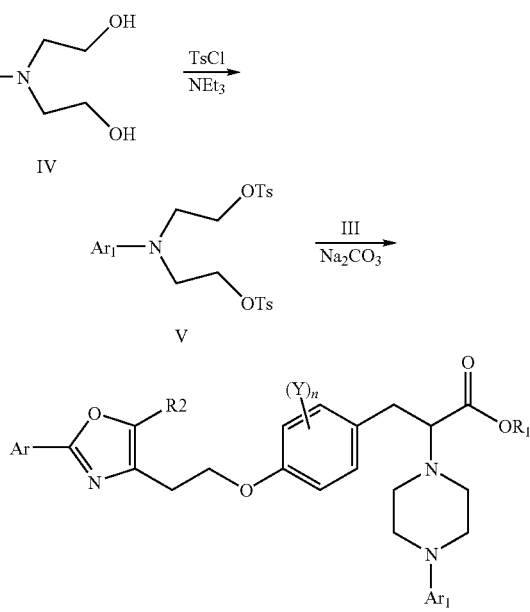

A compound of formula IV (wherein Ar$_1$ is the same as defined above for formula I), which is commercially available or prepared according to the method reported in the literatures (see: Palmer, B. D., et al, Synth Commun 1987, 17, 601; GRAVATT, G. L., et al, J. Med. Chem. 1991, 34 (5), 1552-1560), p-toluenesulfonyl chloride (TSCl) and triethylamine are dissolved in anhydrous dichloromethane, and react at 0° C. for 1 to 20 h. The reaction mixture is washed with water and saturated brine in turn, and dried, followed by concentration and recrystallization with ethanol to obtain the compound of formula V (wherein Ar$_1$ is the same as defined above for formula I). The compound of formula V and the compound of formula III, that is prepared according to the Scheme 1, are dissolved in hexamethylphosphoramide (HMPA), to which anhydrous sodium carbonate is added, before reacting at 130-140° C. for 1 to 10 h. The reaction mixture is purified with silica gel column chromatography (using n-hexane/EtOAc as an eluent) to give a compound of formula I (wherein $Ar_1$, Ar, $R_1$, $R_2$, Y and n are the same as defined above for formula I) as brown oil.

Scheme 3: Synthesis of the compound of formula I where $R_3$ is —$SO_2Ar_1$

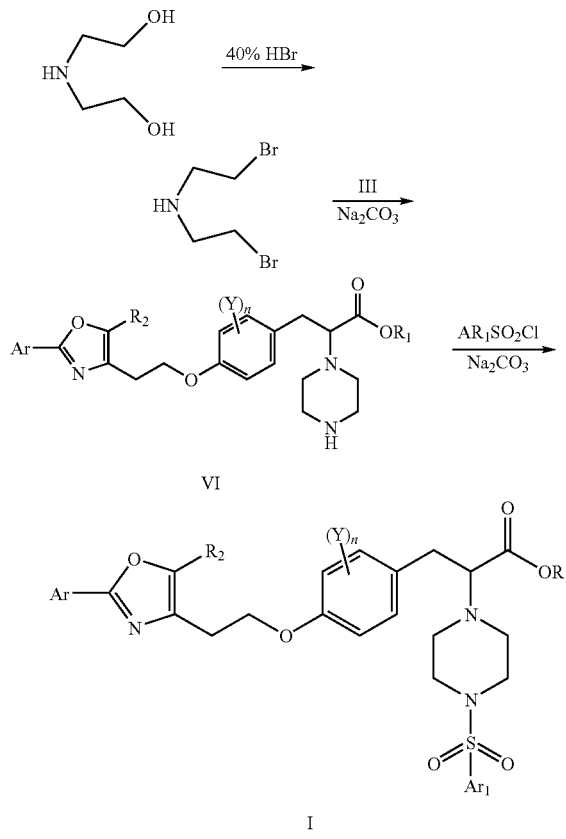

Diethanolamine reacts with 48% HBr aqueous solution at 100-130° C. for 6 to 12 h. During the reaction, water is removed in vacuum continuously. The reaction solution is concentrated to obtain N,N-bis-(2-bromoethyl)-amine hydrobromate as brown oil. Subsequently, N,N-bis-(2-bromoethyl)-amine hydrobromate reacts with the compound of formula III, that is prepared according to the Scheme 1, for 8 to 60 h under the condition of reflux in anhydrous ethanol in the presence of anhydrous sodium carbonate as catalyst. The reaction mixture is concentrated, dissolved in dichloromethane, and washed with water, followed by drying, concentration and purification with silica gel column chromatography (using $CHCl_3$/MeOH as an eluent) to give the compound of formula I (wherein $Ar_1$, Ar, $R_1$, $R_2$, Y and n are the same as defined above for formula I) as brown oil.

If desired, a compound of formula I can be converted to another compound of formula I in a different form. For example, the compound of formula I where $R_1$ represents hydrogen is prepared by reacting the compound of formula I wherein $R_1$ represents $C_1$-$C_4$ straight or branched alkyl with an aqueous solution of alkali metal hydroxide in an organic solvent such as THF or ethanol at room temperature or under the condition of reflux for 0.1 to 20 h, before treating.

Those skilled in the art shall recognize that the compound of formula I has a stereocenter. When a compound of formula I is desired as a single enantiomer, it is prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, for resolving the diastereomeric salts formed with chiral acids such as mandelic acid, camphorsulfonic acid, tartaric acid, lactic acid, and the like wherever applicable or with chiral bases such as brucine, cinchona alkaloids and their derivatives and the like. Commonly used methods are listed in "Enantiomers, Racemates and Resolution" (Wiley Interscience, 1981) as compiled by Jaques, et al. More specifically, the compound of formula I may be converted to a 1:1 mixture of diastereomeric amides by treating with chiral amines, amino acids, or amino alcohols derived from amino acids; an acid may be converted into an amide by using conventional reaction conditions; diastereomers may be separated either by fractional crystallization or chromatography, and stereoisomers of the compound of formula I may be prepared by hydrolysing pure diastereomeric amides.

According to the present invention, the compound of formula I can be used for the treatment or prevention of hPPARγ and/or hPPARα mediated diseases, risk factors or conditions. The hPPARγ and/or hPPARα mediated diseases, risk factors, or conditions include hyperglycemia, dyslipidemia, type II diabetes mellitus including associated diabetic dyslipidemia, type I diabetes, hypertriglyceridemia, syndrome X, insulin resistance, heart failure, hyperlipidemia, hypercholesteremia, hypertension, cardiovascular disease including atherosclerosis, regulation of appetite and food intake in subjects suffering from conditions such as obesity, anorexia, anorexia bulimia, and anorexia nervosa. In particular, the compound of the present invention is useful in the treatment or prevention of hyperglycaemia, dyslipidemia, and type II diabetes mellitus including associated diabetic dyslipidemia.

The compounds of the present invention may be utilized by themselves, or in the form of pharmaceutically acceptable salts or solvates thereof. The physiologically acceptable salts of the compound of formula I include conventional salts formed from pharmaceutically acceptable inorganic or organic acids or bases as well as quaternary ammonium acid addition salts. The specific examples of suitable acid addition salts include hydrochloric, hydrobromic, sulfuric, phosphoric, nitric, perchloric, fumaric, acetic, propionic, succinic, glycolic, formic, lactic, malefic, tartaric, citric, pamoic, malonic, hydroxymaleic, phenylacetic, glutamic, benzoic, salicylic, fumaric, toluenesulfonic, methanesulfonic, naphthalene-2-sulfonic, benzenesulfonic hydroxynaphthoic, hydroiodic, malic, steroic, tannic and the like. Other acids such as oxalic, while not in themselves pharmaceutically acceptable, may be used to prepare salts useful as intermediates for obtaining the compounds of the invention and their pharmaceutically acceptable salts. The specific examples of suitable basic salts include sodium, lithium, potassium, magnesium, aluminum, calcium, zinc, N,N'-dibenzylethylenediamine, chloroprocaine, choline, diethanolamine, ethylenediamine, N-methylglucamine and procaine salts. References to a compound according to the invention include both compounds of formula I and their pharmaceutically acceptable salts or solvates.

The invention also includes prodrugs of the present compounds, which upon administration undergo chemical conversion by metabolic processes in vivo before becoming active drugs. In general, such prodrugs are functional derivatives of the present compounds, which are readily convertible in vivo into the required compound of formula I. Conventional procedures for the selection and preparation of suitable prodrug derivatives are described, for example, in "Design of Prodrugs", ed. H. Bundgaard, Elsevier, 1985.

The invention also includes active metabolites of the present compounds.

The present compounds can be utilized alone or in the form of pharmaceutical composition. The pharmaceutical composition comprises an effective amount of a compound of formula I, a racemate, an optically active isomer, or a pharmaceutically acceptable salt or solvate thereof, and one or more suitable pharmaceutically acceptable carriers. The pharmaceutically acceptable carrier is selected from, but is not limited to, ion exchanger, aluminum oxide, aluminum stearate, lecithin, serum protein (e.g. human serum protein), buffer substance (e.g. phosphate), glycerol, sorbic acid, potassium sorbate, mixture of partial glycerides of saturated vegetable fatty acids, water, salt or electrolyte (e.g. protamine sulfate, disodium hydrogen phosphate, potassium hydrogen phosphate, sodium chloride, zinc salt), colloidal silicon oxide, magnesium trisilicate, polyvinylpyrrolidone, cellulose, polyethylene glycol, carboxymethycellulose sodium, polyacrylate, beeswax, and lanolin.

The pharmaceutical composition comprising the compound according to the invention may be administered orally, by inhalation spray, rectally, nasally, buccally, topically, parenterally (such as, subcutaneous, intravenous, intramuscular, intraperitoneal, intrachecal, intraventricular, intrasteral, and intracranial injection or infusion), or via an implanted reservoir, preferably orally, intraperitoneally, or intravenously.

When administered orally, the compound of the invention may be produced in any orally acceptable formulation forms comprising, but being not limited to, tablets, capsules, aqueous solutions or aqueous suspensions. Typically, the carriers used for tablets include lactose and corn starch. In addition, lubricating agents such as magnesium stearate may also be added. Usually, diluents used for capsules include lactose and dried corn starch. Aqueous suspension formulations generally include mixture of suitable emulsifying and suspending agents with the active ingredient. If desired, the oral formulation forms may further comprise sweetening agents, flavoring agents or coloring agents.

When administered topically, especially when the conditions addressed for treatment involve areas or organs readily accessible by topical application, including neurological conditions of eye, skin, or lower intestinal tract, the compounds of the invention may be prepared into different topical administration formulations in accordance with the areas or organs.

For topical application to eyes, the compounds of the invention can be formulated as micronized suspensions or solutions in isotonic, pH adjusted sterile saline, either with or without a preservative such as benzylalkonium chloride. Alternatively, for the ophthalmic uses, the compounds may also be formulated in an ointment such as petrolatum.

For topical application to the skin, the compounds can be formulated in a suitable ointment, lotion or cream, wherein the active ingredient suspends or dissolves in one or more carriers. The carriers suitable for ointment include, but are not limited to, mineral oil, liquid petrolatum, white petrolatum, propylene glycol, polyoxyethylene, polyoxypropylene, emulsifying wax and water; and the carriers suitable for lotion or cream include, but are not limited to, mineral oil, sorbitan monostearate, Tween 60, cetyl ester wax, cetearyl alcohol, 2-octyldodecanol, benzyl alcohol and water.

The compounds of the present invention may be administered in the form of sterile injection preparations, for example, as sterile injection aqueous or oleaginous suspensions or sterile injection solutions. The acceptable carriers and solvents include water, Ringer's solution and isotonic sodium chloride solution. In addition, sterile, fixed oils, such as mono- or di-glycerides, can be also employed as solvents or suspending mediums.

In addition, the dosage level and usage method of the present compound depend upon a variety of factors including, the age, body weight, gender, natural health condition, and nutritional status of the subject, the activity of the specific compound employed, the time of administration, the rate of metabolism, the severity of the particular disease being treated, and the subjective judgment of the doctor for diagnosis. The dosage levels on the order of about 0.01 mg to about 100 mg of the active ingredient/kg body weight/day are preferred, while the optimal dosage levels are 5 mg to 10 mg of the active ingredient/kg body weight/day.

MODE OF CARRYING OUR THE INVENTION

The following examples are preferred illustrative examples of the invention, which do not intend to limit the present invention.

Melting points are determined with a RY-1 melting point apparatus and the temperatures are not rectified. $^1$H NMR spectra are recorded on a Bruker ARX 400 NMR spectrometer or on a US Varian Ulity Inova 600 NMR spectrometer. FAB mass spectra were recorded on a Zabspect high resolution magnetic mass spectrometer.

PREPARATION EXAMPLE 1

2-(5-Methyl-2-phenyl-1,3-oxazol-4-yl)-ethanol (Intermediate 1)

Methyl 4-bromo-3-pentanoate (23.2 g, 0.11 mol) and benzamide (20.1 g, 0.17 mol) were dissolved in 160 mL of toluene, and heated to reflux for 9 h. The water produced during the reaction was removed with a delivery bead. The crude product obtained was purified with silica gel column chromatography (using n-hexane/EtOAc (6/1) as an eluent) to give 5.6 g of 2-(5-methyl-2-phenyl-1,3-oxazol-4-yl)-acetic acid methyl ester as light brown oil with a yield of 22%.

2-(5-Methyl-2-phenyl-1,3-oxazol-4-yl)-acetic acid methyl ester (2.3 g, 10 mmol) was dissolved in 16 mL of Et$_2$O, and then added dropwise at 0° C. to a suspension of LiAlH$_4$ (0.38 g, 10 mmol) in Et$_2$O (4 mL). The solution was stirred at room temperature overnight, to which 0.4 mL H$_2$O, 0.4 mL of 15% NaOH solution, and 1.2 mL of H$_2$O, and a spoon of anhydrous MgSO$_4$ were carefully added in turn. The mixture was filtered, and the filtrate was concentrated to give 1.6 g of 2-(5-methyl-2-phenyl-1,3-oxazol-4-yl)-ethanol as a light yellow solid with a yield of 80%.

MS[M]+=231.2 m/e;

$^1$H-NMR (400 MHz, CDCl$_3$), δ 7.99~7.78 (m, 2H), 7.43~7.42 (m, 3H), 3.94 (t, 2H), 2.74 (t, 2H), 2.34 (s, 3H).

PREPARATION EXAMPLE 2A (2S)-2-tert-butoxycarbonylamino-3-(4-hydroxy-phenyl)-propionic acid methyl ester (Intermediate 2A)

At 0° C., thionyl chloride (8 mL, 0.11 mmol) was added dropwise to a solution of methanol (100 mL) containing L-tyrosine (17.9 g, 0.1 mmol), before refluxing for 3 h. The resulting solution was concentrated, to which triethylamine (15 mL) and acetonitrile (150 mL) were added, followed by dropping of di-tert-butyl dicarbonate (BOC$_2$O) (23.3 mL, 0.11 mol). Thereafter, the mixture was stirred for 1.5 h at room temperature. After concentration, the mixture was dissolved with dichloromethane (200 mL), and then washed with 1M NaHSO$_4$ aqueous solution (200 mL), a little of saturated sodium carbonate aqueous solution and water in turn. The organic layer was then dried over anhydrous MgSO$_4$, followed by concentration to give 26 g of (2S)-2-tert-butoxycarbonylamino-3-(4-hydroxy-phenyl)-propionic acid methyl ester as a white solid with a yield of 90%.

MS[M]+=295.4 m/e;

$^1$H-NMR (400 MHz, CDCl$_3$), δ 6.98~6.90 (m, 2H), 6.78~6.73 (m, 2H), 4.60~4.50 (m, 1H), 3.70 (s, 3H), 3.08~2.93 (m, 2H), 1.45 (s, 9H).

PREPARATION EXAMPLE 2B (2S)-3-(3-Bromo-4-hydroxy-phenyl)-2-tert-butoxycarbonylamino-propionic acid methyl ester (Intermediate 2B)

At 0° C., a solution of bromine (0.9 g, 5.5 mmol) in glacial acetic acid (8 mL) was added dropwise to a suspension of L-tyrosine (1.0 g, 5.5 mmol) in glacial acetic acid (10 mL). The solution was stirred at room temperature overnight. The resulting mixture was filtered, and the filter cake was dried to obtain 1.7 g of a white solid, which was used directly in the next reaction.

The reaction was carried out by following the procedures described in Preparation Example 2A. The obtained crude product was further purified by silica gel column chromatography (using petroleum ether/EtOAc (4/1) as an eluent) to give 0.8 g of Intermediate 2B as white solid with a yield of 38.6%.

MS[M]+=374.4 m/e;

$^1$H-NMR (400 MHz, DMSO-d$_6$), δ7.37 (d, 1H), 7.10~7.05 (dd, 2H), 3.56 (s, 3H), 3.52~2.50 (m, 1H), 2.80~2.65 (m, 2H), 1.45 (s, 9H).

PREPARATION EXAMPLE 3A (2S)-2-amino-3-4-[2-(5-methyl-2-phenyl-1,3-oxazol-4-yl)ethoxy]-phenyl}-proponic acid methyl ester (Intermediate 3A)

Intermediate 1 (10.1 g, 0.05 mol), intermediate 2A (14.7 g, 0.05 mol) and triphenylphosphine (14.41 g, 0.055 mol) were dissolved with dried THF (180 mL), to which a solution of 40% diethyl azodicarboxylate (DIAD, 0.14 mol) in toluene (74 mL) was dropped. The mixture was stirred at room temperature for 20 h before concentration. The residue was purified by silica gel column chromatography (using petroleum ether/EtOAc (3/1) as an eluent) to give 16.8 g of (2S)-2-tert-butoxycarbonylamino-3-{4-[2-(5-methyl-2-phenyl-1,3-oxazol-4-yl)-ethoxy]-phenyl}-propionic acid methyl ester as light yellow oil with a yield of 67%.

(2S)-2-tert-Butoxycarbonylamino-3-{4-[2-(5-methyl-2-phenyl-1,3-oxazol-4-yl)-ethoxy]-phenyl}-propionic acid methyl ester (16.8 g, 0.035 mol), trifluoroacetic acid (34 mL) and dichloromethane (340 mL) were mixed with stirring at room temperature overnight. The mixture was neutralized with 0.5% NaOH aqueous solution. The organic layer was dried over anhydrous sodium sulfate, and then concentrated. The residue was purified by silica gel column chromatography (using CHCl$_3$/MeOH (80/1) as an eluent) to give 10.6 g of Intermediate 3A as light brown oil with a yield of 80%.

MS[M]+=380.4 m/e;

$^1$H-NMR (400 MHz, DMSO-d$_6$), δ 7.92~7.89 (m, 2H), 7.52~7.45 (m, 3H), 7.07 (d, 2H), 6.83 (d, 2H), 4.17 (t, 2H), 3.56 (s, 3H), 3.51~3.42 (m, 1H), 2.93 (t, 2H), 2.80~2.67 (m, 2H), 2.36 (s, 3H), 1.75 (s, 2H).

PREPARATION EXAMPLE 3B (2S)-2-amino-3-{3-bromo-4-[2-(5-methyl-2-phenyl-1,3-oxazol-4-yl)-ethoxy]-phenyl}-propionic acid (Intermediate 3B)

Following the procedures described in the preparation of Intermediate 3A, intermediate 2B was used in place of intermediate 2A to give (2S)-2-amino-3-{3-bromo-4-[2-(5-methyl-2-phenyl-1,3-oxazol-4-yl)-ethoxy]-phenyl}-propionic acid.

MS[M]+=459.4 m/e;

$^1$H-NMR (400 MHz, DMSO-d$_6$), δ 7.92~7.89 (m, 2H), 7.52~7.48 (m, 3H), 7.37 (d, 1H), 7.10~7.05 (dd, 2H), 4.25 (t, 2H), 3.56 (s, 3H), 3.52~2.50 (m, 1H), 2.94 (t, 2H), 2.80~2.65 (m, 2H), 2.38 (s, 3H), 1.76 (s, 2H).

PREPARATION EXAMPLE 4

(2S)-3-{4-[2-(5-methyl-2-phenyl-1, 3-oxazol-4-yl)-ethoxy]-phenyl}-2-piperazin-1-yl-propionic acid methyl ester (Intermediate 4)

Diethanolamine (100 g) and 40% HBr aqueous solution (1000 mL) were mixed and vigorously refluxed for 10 h, while water was removed continuously under reduced pressure during the reaction. The resulting solution was concentrated to give 297 g of a brown liquid.

The above brown liquid (47.4 g), Intermediate 3A (4.5 g, 11.8 mmol) and 150 mL of anhydrous ethanol were mixed with refluxing overnight. Thereafter, the mixture was cooled to room temperature, to which Na$_2$CO$_3$ (1.3 g, 11.8 mmol) was added before further refluxing for 10 h. After cooling to room temperature, the mixture was filtered and evaporated to remove ethanol. The residue was dissolved in CHCl$_3$, and washed with water and saturated brine in turn, and then dried over anhydrous Na$_2$SO$_4$. After concentration and purification with silica gel column chromatography (using CHCl$_3$/CH$_3$OH (60/1) as an eluent), Intermediate 4A (1.0 g, 24% yield) as a brown solid was obtained.

MS[M]+=449.4 m/e;

$^1$H-NMR (400 MHz, DMSO-d$_6$), δ 7.98~7.96 (m, 2H), 7.46~7.38 (m, 3H), 7.06 (d, 2H), 6.81 (d, 2H), 2.70~2.61 (m, 2H), 2.60~2.51 (m, 2H), 2.36 (s, 3H).

EXAMPLE 1

(2S)-3-{4-[2-(5-methyl-2-phenyl-1,3-oxazol-4-yl)-ethoxy]-phenyl}-2-(4-m-tolyl-piperazin-1-yl)-propionic acid At 0° C. and under the protection of $N_2$, 2,2'-(m-tolylazanediyl)diethanol (1.0 g, 5.13 mmol), p-toluene sulfonyl chloride (2.0 g, 10.53 mmol) and triethylamine (1.1 g, 10.89 mmol) were mixed and dissolved in anhydrous $CH_2Cl_2$ with stirring for 30 min and then put in a refrigerator overnight. The reaction mixture was washed with water and saturated brine, and dried over anhydrous sodium sulfate. After concentration, a suitable amount of ethanol was added to the residue, followed by naturally standing to give 0.9 g of a white solid.

The white solid as above obtained, Intermediate 3A (0.6 g, 1.58 mmol) and $NaHCO_3$ (0.27 g, 3.21 mmol) were mixed in HMPA (4 mL), and reacted by heating to 134° C. for 4 h. The reaction mixture was separated by silica gel column chromatography (using n-hexane/EtOAc (5/1) as an eluent), and concentrated to give a colorless heavy-bodied matter. The heavy-bodied matter was dissolved in THF, to which excessive 1N LiOH aqueous solution was added dropwise, before stirring at room temperature overnight. The resulting solution was acidified to pH 2-3 with 2N diluted HCl solution, and extracted for three times with $CHCl_3$. The organic layer was dried over anhydrous $Na_2SO_4$, concentrated and then recrystallized with anhydrous ethanol to give 0.54 g of a white solid with a yield of 20% and mp of 205~207° C.

$MS[M]+=525.4$ m/e;

$^1$H-NMR (400 MHz, DMSO-$d_6$), δ 7.95~7.90 (m, 2H), 7.55~7.45 (m, 3H), 7.20~7.04 (m, 3H), 6.90~6.58 (m, 5H), 4.18 (t, 2H, J=6.6 Hz), 3.45~3.44 (m, 1H), 3.20~3.00 (m, 4H), 2.90 (t, 2H), 2.90~2.64 (m, 6H), 2.35 (s, 3H), 2.22 (s, 3H).

EXAMPLE 2

(2S)-2-[4-(4-nitro-benzenesulfonyl)-piperazin-1-yl]-3-{4-[2-(5-methyl-2-phenyl-1,3-oxazol-4-yl)-ethoxy]-phenyl}-propionic acid Intermediate 4A (0.31 g, 0.69 mmol), 4-nitro-benzenesulfonyl chloride (0.19 g, 0.86 mmol) and $Et_3N$ (0.21 g, 2.1 mmol) were dissolved in anhydrous $CH_2Cl_2$ (6 mL) with stirring at room temperature overnight. The mixture was separated by column chromatography (using petroleum ether/EtOAc (3/1) as an eluent), and concentrated to give a brown sticky matter (0.15 g). The sticky matter was dissolved in THF, to which excessive 1N LiOH aqueous solution was added dropwise, before stirring at room temperature overnight. The resulting solution was acidified to pH 2-3 with 2N HCl solution, and extracted for three times with $CHCl_3$. The organic layer was washed with saturated brine, dried over anhydrous $Na_2SO_4$, concentrated and then recrystallized with THF to give 0.13 g of a yellow solid with a yield of 30% and mp of 205~207° C.

$MS[M]+=620.4$ m/e;

$^1$H-NMR (400 MHz, DMSO-$d_6$), δ 8.43~8.41 (m, 2H), 8.02~8.00 (m, 2H), 7.88~7.86 (m, 2H), 7.48~7.46 (m, 3H), 7.08~7.06 (d, 2H), 6.81~6.79 (d, 2H), 4.17 (t, 2H), 3.56 (m, 1H), 3.10~2.86 (m, 12H), 2.32 (s, 3H).

EXAMPLE 3

(2S)-2-[4-(2-fluoro-benzenesulfonyl)-piperazin-1-yl]-3-{4-[2-(5-methyl-2-phenyl-1,3-oxazol-4-yl)-ethoxy]-phenyl}-propionic acid Following the procedures described in Example 2, 2-fluorobenzene-1-sulfonyl chloride was used in place of 4-nitrobenzene-1-sulfonyl chloride to give (2S)-2-[4-(2-fluoro-benzenesulfonyl)-piperazin-1-yl]-3-{4-[2-(5-methyl-2-phenyl-1,3-oxazol-4-yl)-ethoxy]-phenyl}-propionic acid as a white solid with the yield of 28% and mp of 170-172° C.

$MS[M+H]^+=593.2$ m/e;

$^1$H-NMR (DMSO-$d_6$, 400 MHz): δ 12.79 (brs, 1H), 7.92~7.89 (m, 2H), 7.78~7.74 (m, 2H), 7.51~7.41 (m, 5H), 7.07~7.05 (d, 2H, J=8.5 Hz), 6.80~6.78 (d, 2H, J=8.5 Hz), 4.17 (t, 2H, J=6.6 Hz), 3.35 (m, 1H), 3.10~2.49 (m, 12H), 2.33 (s, 3H).

EXAMPLE 4

(2S)-2-[4-(4-fluoro-benzenesulfonyl)-piperazin-1-yl]-3-{4-[2-(5-methyl-2-phenyl-1,3-oxazol-4-yl)-ethoxy]-phenyl}-propionic acid Following the procedures described in Example 2, 4-fluorobenzene-1-sulfonyl chloride was used in place of 4-nitrobenzene-1-sulfonyl chloride to give (2S)-2-[4-(4-fluoro-benzenesulfonyl)-piperazin-1-yl]-3-{4-[2-(5-methyl-2-phenyl-1,3-oxazol-4-yl)-ethoxy]-phenyl}-propionic acid as a white solid with the yield of 32% and mp of 198-200° C.

$MS[M+H]^+=594.2$ m/e:

$^1$H-NMR (DMSO-$d_6$, 400 MHz): δ 7.80~7.95 (m, 4H), 7.55~7.45 (m, 5H), 7.10 (d, 2H), 6.80 (d, 2H), 4.80~4.70 (m, 1H), 4.15 (t, 2H, J=6.6 Hz), 3.10~2.82 (m, 12H), 2.30 (s, 3H).

EXAMPLE 5

(2S)-2-[4-benzenesulfonyl-piperazin-1-yl]-3-{4-[2-(5-methyl-2-phenyl-1,3-oxazol-4-yl)-ethoxy]-phenyl}-propionic acid Following the procedures described in Example 2, benzenesulfonyl chloride was used in place of 4-nitrobenzene-1-sulfonyl chloride to give (2S)-2-[4-benzenesulfonyl-piperazin-1-yl]-3-{4-[2-(5-methyl-2-phenyl-1,3-oxazol-4-yl)-ethoxy]-phenyl}-propionic acid as a white solid with the yield of 23% and mp of 180-182° C.

$MS[M+H]+=575.4$ m/e;

$^1$H-NMR (DMSO-$d_6$, 400 MHz): δ 7.93~7.90 (m, 2H), 7.60~7.59 (m, 2H), 7.51~7.44 (m, 5H), 7.06~7.04 (d, 2H, J=8.7 Hz), 6.80~6.77 (d, 2H, J=8.7 Hz), 4.14 (t, 2H, J=6.6 Hz), 3.50~3.40 (m, 1H), 3.10~2.78 (m, 12H), 2.40 (s, 3H), 2.35 (s, 3H).

EXAMPLE 6

(2S)-2-[4-(2-nitro-benzenesulfonyl)-piperazin-1-yl]-3-{4-[2-(5-methyl-2-phenyl-1,3-oxazol-4-yl)-ethoxy]-phenyl}-propionic acid Following the procedures described in Example 2, 2-nitrobenzene-1-sulfonyl chloride was used in place of 4-nitrobenzene-1-sulfonyl chloride to give (2S)-2-[4-(2-nitrobenzenesulfonyl)-piperazin-1-yl]-3-{4-[2-(5-methyl-2-phenyl-1,3-oxazol-4-yl)-ethoxy]-phenyl}-propionic acid as a white solid with the yield of 24% and mp of 171-173° C.

MS[M+H]$^+$=620.4 m/e;

$^1$H-NMR (DMSO-d$_6$, 400 MHz): δ 12.42 (brs, 1H), 7.97~7.91 (m, 6H), 7.50~7.48 (m, 3H), 7.07 (m, 2H), 6.81~6.79 (m, 2H), 4.15 (t, 2H, J=6.6Hz), 3.31 (m, 1H), 3.12 (m, 4H), 2.89~2.80 (m, 3H), 2.72 (m, 3H), 2.58 (m, 2H), 2.33 (s, 3H).

EXAMPLE 7

(2S)-2-[4-(m-chloro-phenyl)-piperazin-1-yl]-3-{4-[2-(5-methyl-2-phenyl-1,3-oxazol-4-yl)-ethoxy]-phenyl}-propionic acid;

Following the procedures described in Example 1, 2,2'-(3-chlorophenylazanediyl)diethanol was used in place of 2,2'-(m-tolylazanediyl)diethanol to give (2S)-2-[4-(m-chloro-phenyl)-piperazin-1-yl]-3-{4-[2-(5-methyl-2-phenyl-1,3-oxazol-4-yl)-ethoxy]-phenyl}-propionic acid as a white solid with the yield of 20% and mp of 138-139° C.

MS[M+H]$^+$=546.2 m/e;

$^1$H-NMR (DMSO-d$_6$, 400 MHz): δ 7.91 (m, 2H), 7.53~7.48 (m, 3H), 7.26~7.15 (m, 3H), 6.97 (s, 1H), 6.93~6.83 (m, 5H), 4.20 (t, 2H, J=6.6Hz), 3.80 (m, 1H), 3.34 (m, 4H), 3.12 (m, 5H), 2.98~2.90 (m, 3H), 2.35 (s, 3H).

EXAMPLE 8

(2S)-3-{4-[2-(5-methyl-2-phenyl-1,3-oxazol-4-yl)-ethoxy]-phenyl}-2-(4-phenyl-piperazin-1-yl)-propionic acid;

Following the procedures described in Example 1, 2,2'-(phenylazanediyl)diethanol was used in place of 2,2'-(m-tolylazanediyl)diethanol to give (2S)-3-{4-[2-(5-methyl-2-phenyl -1,3-oxazol-4-yl)-ethoxy]-phenyl}-2-(4-phenyl-piperazin-1-yl)-propionic acid as a white solid with the yield of 27% and mp of 218-220° C.

MS[M+H]$^+$=512.3 m/e;

$^1$H-NMR (DMSO-d$_6$, 400 MHz): δ 7.92~7.89 (m, 2H), 7.53~7.45 (m, 3H), 7.25~7.15 (m, 4H), 6.95~6.81 (m, 5H), 4.20 (t, 2H, J=6.6 Hz), 3.83~3.72 (brs, 1H), 3.30~2.90 (m, 12H), 2.36 (s, 3H).

EXAMPLE 9

(2S)-3-{3-bromo-4-[2-(5-methyl-2-phenyl-1,3-oxazol-4-yl)-ethoxy]-phenyl}-2-(4-p-tolyl-piperazin-1-yl)-propionic acid; and Following the procedures described in Example 1, Intermediate 3B was used in place of Intermediate 3A, and 2,2'-(p-tolylazanediyl)diethanol was used in place of 2,2'-(m-tolylazanediyl)diethanol to give (2S)-3-{3-bromo-4-[2-(5-methyl-2-phenyl-1,3-oxazol-4-yl)-ethoxy]-phenyl}-2-(4-p-tolyl-piperazin-1-yl)-propionic acid as a white solid with the yield of 24% and mp of 203-205° C.

MS[M+H]$^+$=525.2 m/e;

$^1$H-NMR (DMSO-d$_6$, 400 MHz): δ 7.92~7.90 (m, 2H), 7.49~7.48 (m, 3H), 7.14~7.12 (m, 2H), 7.01~6.99 (m, 2H), 6.84~6.80 (m, 4H), 4.18 (t, 2H, J=5.8 Hz), 3.36~3.34 (m, 1H), 3.04~2.66 (m, 12H), 2.35 (s, 3H), 2.19 (s, 3H).

EXAMPLE 10

(2S)-3-{3-bromo-4-[2-(5-methyl-2-phenyl-1,3-oxazol-4-yl)-ethoxy]-phenyl}-2-(4-phenylpiperazin-1-yl)-propanoic acid;

Following the procedures described in Example 1, Intermediate 3B was used in place of Intermediate 3A, and 2,2'-(phenylazanediyl)diethanol was used in place of 2,2'-(m-tolylazanediyl)diethanol to give (2S)-3-{3-bromo-4-[2-(5-methyl-2-phenyl-1,3-oxazol-4-yl)-ethoxy]-phenyl}-2-(4-phenylpiperazin-1-yl)-propanoic acid as a white solid with the yield of 30% and mp of 220-222° C.

MS[M+H]$^+$=590.2 m/e;

$^1$H-NMR (DMSO-d$_6$, 400 MHz): δ 7.94~7.90 (m, 2H), 7.51~7.47 (m, 4H), 7.26~7.22 (m, 3H), 7.10~6.82 (m, 4H), 4.26 (t, 2H, J=6.4 Hz), 3.85 (brs, 1H), 3.29~2.92 (m, 12H), 2.35 (s, 3H).

EXAMPLE 11

Activity Assay of Compounds on Activating Human PPARα and PPARγ

The compounds were screened with respect to their functional effect of instantaneous transfection in 293-T cells, so that their capabilities of activating PPAR subtypes were determined. A chimeric receptor system as established in advance was used to compare the influence of receptor subtypes on the transcription activity of same target gene. Human PPARα and PPARγ ligand-binding domains were fused respectively with yeast transcription factor GAL4 DNA-binding domains, and then linked to expression vector pM of mammal, to thereby construct two plasmids pM-hPPARα/GAL4 and pM-PPARγ/GAL4. GAL4 DNA-binding area was linked to pB4-tk-luc, to thereby construct pB4-RES-tk-luc (a firefly luciferase reporter gene comprising GAL4 DNA-binding site). pRL-CMV-Rluc was used as an internal control to normalize transfection efficiency and endogenous influence.

293-T cells were incubated in a 48-well plate at a cell density of 2-4×10$^4$/well, using a phenol red-free and antibiotic-free 1640 medium containing 10% defatted fetal calf serum (FCS). After culturing for 48 h, the medium was replaced with a phenol red-free and antibiotic-free 1640 medium containing 5% defatted FCS, and then three plasmids pM-hPPAR/GAL4, pB4-RES-tk-luc and pRL-CMV-Rluc pertaining to two subtypes were respectively co-transfected into the 293-T cells. The strength of luciferase was measured at the time of 24 h after administration, with 0.2% DMSO as a blank control.

Effect of compounds (10 μM) on activation of PPARα and EC$_{50}$ Value

| Compound | Photon number (×10$^4$) | Increased multiple vs control | EC$_{50}$ (μM) |
|---|---|---|---|
| DMSO control | 2.1 | | |
| Example 1 | 11.3 | 5.3 | |
| Example 3 | 5.3 | 2.5 | |
| Example 4 | 6.8 | 3.2 | |
| Example 6 | 26.3 | 12.5 | 1.05 |
| Example 8 | 13.2 | 6.3 | |

Effect of compounds (10 μM) on activation of PPARγ and $EC_{50}$ Value

| Compound | Photon number (×10⁴) | Increased multiple vs control | $EC_{50}$ (μM) |
|---|---|---|---|
| Control | 1.4 | | |
| Example 1 | — | — | |
| Example 3 | 13.6 | 9.7 | |
| Example 4 | 2.8 | 2.0 | |
| Example 6 | 21.0 | 15.0 | 3.20 |
| Example 8 | — | — | |

The invention claimed is:

1. A compound of formula I, racemate, optically active isomer, or pharmaceutically acceptable salt thereof,

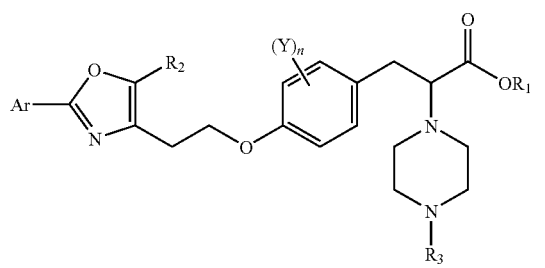

I wherein:
$R_1$ and $R_2$ are independently hydrogen, or $C_{1-4}$ straight or branched alkyl;
$R_3$ is $Ar_1$ or —$SO_2Ar_1$;
Ar and $Ar_1$ are phenyl ring which is unsubstituted or optionally substituted with 1 to 5 of the following groups: halogen, nitro, hydroxy, hydroxymethyl, trifluoromethyl, trifluoromethoxy, $C_1$-$C_6$ straight or branched alkyl, $C_2$-$C_6$ straight or branched alkenyl, $C_1$-$C_4$ alkoxy, $C_2$-$C_4$ alkenoxy, phenoxy, benzyloxy, carboxyl or amino;
Y is hydrogen or halogen; and
n is an integer from 1 to 4.

2. The compound of claim 1, which is in S-configuration isomer of formula II,

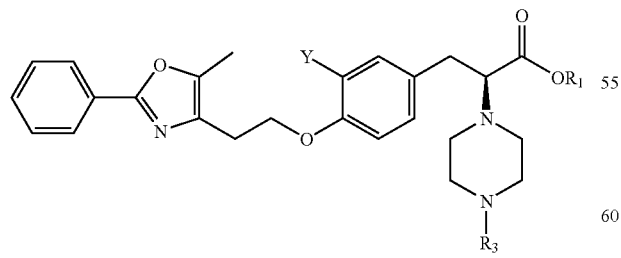

II wherein:
carbon atom bonded to $COOR_1$ is in the S configuration
$R_1$ is hydrogen or methyl;
$R_3$ is $Ar_1$ or —$SO_2Ar_1$;
$Ar_1$ is phenyl ring which is unsubstituted or optionally substituted with 1 to 5 of the following groups: halogen, nitro, hydroxy, hydroxymethyl, trifluoromethyl, trifluoromethoxy, $C_1$-$C_6$ straight or branched alkyl, $C_2$-$C_6$ straight or branched alkenyl, $C_1$-$C_4$ alkoxy, $C_2$-$C_4$ alkenoxy, phenoxy, benzyloxy, carboxyl or amino; and
Y is hydrogen or bromo;
or a pharmaceutically acceptable salt thereof.

3. The compound of claim 1, selected from the group consisting of:
(2S)-3-{4-[2-(5-methyl-2-phenyl-1,3-oxazol-4-yl)-ethoxy]-phenyl}-2-(4-m-tolyl-piperazin-1-yl)-propionic acid;
(2S)-2-[4-(4-nitro-benzenesulfonyl)-piperazin-1-yl]-3-{4-[2-(5-methyl-2-phenyl-1,3-oxazol-4-yl)-ethoxy]-phenyl}-propionic acid;
(2S)-2-[4-(2-fluoro-benzenesulfonyl)-piperazin-1-yl]-3-{4-[2-(5-methyl-2-phenyl-1,3-oxazol-4-yl)-ethoxy]-phenyl}-propionic acid;
(2S)-2-[4-(4-fluoro-benzenesulfonyl)-piperazin-1-yl]-3-{4-[2-(5-methyl-2-phenyl-1,3-oxazol-4-yl)-ethoxy]-phenyl}-propionic acid;
(2S)-2-(4-benzenesulfonyl-piperazin-1-yl)-3-{4-[2-(5-methyl-2-phenyl-1,3-oxazol-4-yl)-ethoxy]-phenyl}-propionic acid;
(2S)-2-[4-(2-nitro-benzenesulfonyl)-piperazin-1-yl]-3-{4-[2-(5-methyl-2-phenyl-1,3-oxazol-4-yl)-ethoxy]-phenyl}-propionic acid;
(2S)-2-[4-(m-chloro-phenyl)-piperazin-1-yl]-3-{4-[2-(5-methyl-2-phenyl-1,3-oxazol-4-yl)-ethoxy]-phenyl}-propionic acid;
(2S)-3-{4-[2-(5-methyl-2-phenyl-1,3-oxazol-4-yl)-ethoxy]-phenyl}-2-(4-phenyl-piperazin-1-yl)-propionic acid;
(2S)-3-{3-bromo-4-[2-(5-methyl-2-phenyl-1,3-oxazol-4-yl)-ethoxy]-phenyl}-2-(4-p-tolyl-piperazin-1-yl)-propionic acid; and
(2S)-3-{3-bromo-4-[2-(5-methyl-2-phenyl-1,3-oxazol-4-yl)-ethoxy]-phenyl}-2-(4-phenylpiperazin-1-yl)-propanoic acid;
or pharmaceutically acceptable salts and solvates thereof.

4. A pharmaceutical composition comprising a compound of claim 1, a racemate, an optically active isomer, or a pharmaceutically acceptable salt thereof, and at least one pharmaceutically acceptable carrier.

5. A process for preparing a compound according to claim 1, comprising:
1) reacting a compound of formula IV,

IV

V with p-toluenesulfonyl chloride to obtain a compound of formula V; and 2) reacting the compound of formula V obtained in step 1),

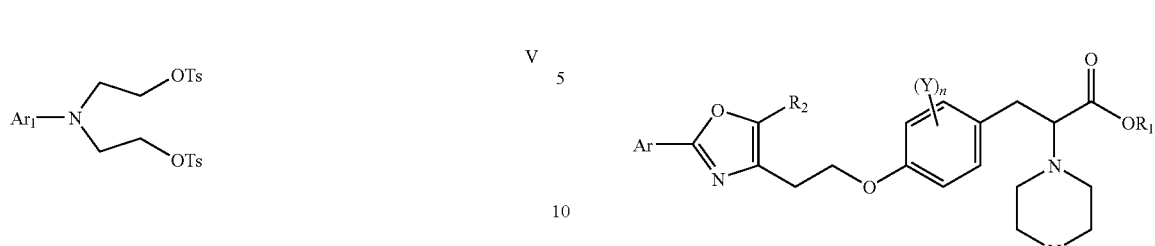

V with a compound of formula III

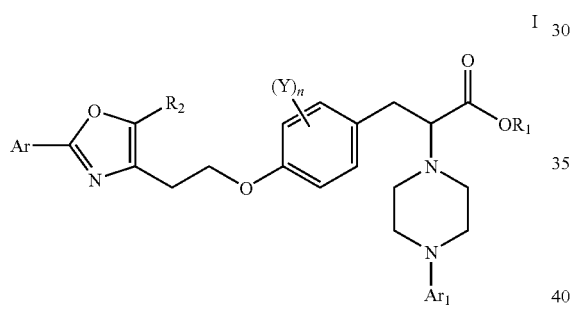

III to obtain the compound of formula I wherein $R_3$ represents $Ar_1$;

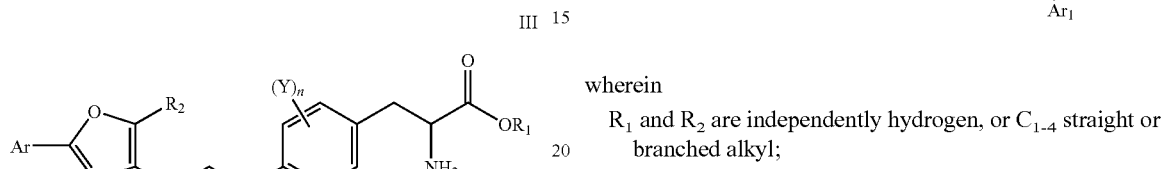

I or 1) reacting the compound of formula III with N,N-bis-(2-bromoethyl)-amine hydrobromate to obtain a compound of formula VI;

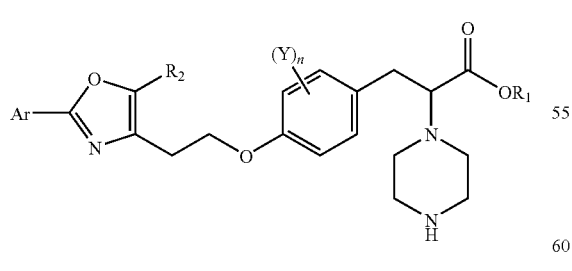

VI and 2) reacting the compound of formula VI with $Ar_1SO_2Cl$ to obtain the compound of formula I wherein $R_3$ represents $-SO_2Ar_1$;

I wherein $R_1$ and $R_2$ are independently hydrogen, or $C_{1-4}$ straight or branched alkyl;

Ar and $Ar_1$ are phenyl ring which is unsubstituted or optionally substituted with 1 to 5 of the following groups: halogen, nitro, hydroxy, hydroxymethyl, trifluoromethyl, trifluoromethoxy, $C_1$-$C_6$ straight or branched alkyl, $C_2$-$C_6$ straight or branched alkenyl, $C_1$-$C_4$ alkoxy, $C_2$-$C_4$ alkenoxy, phenoxy, benzyloxy, carboxyl or amino;

Y is hydrogen or halogen; and n is an integer from 1 to 4.

6. The process of claim 5, further comprising:

reacting a compound of formula I wherein $R_1$ represents $C_1$-$C_4$ straight or branched alkyl with an alkali metal hydroxide to obtain a compound of formula I wherein $R_1$ represents hydrogen.

7. The process of claim 5 wherein the compound of formula III is prepared by the steps of:

1) subjecting an arylformamide and a compound of formula VII to a ring closure reaction, to thereby obtain a compound of formula VIII, reducing the compound of formula VIII with lithium aluminum hydride ($LiAlH_4$) to obtain a compound of formula IX;

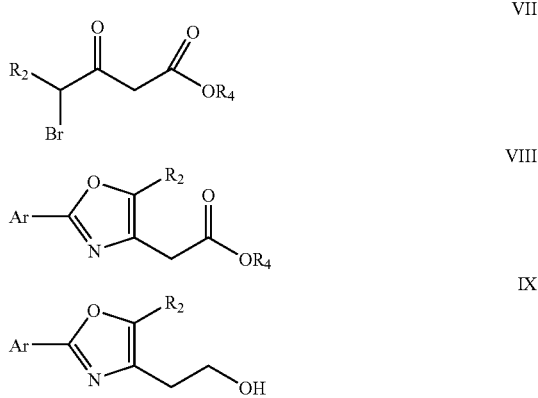

VII

VIII

IX 2) reacting a compound of formula X with $R_1OH$ and reacting obtained residue with $BOC_2O$ under catalysis of triethylamine, to obtain a compound of formula XI; and

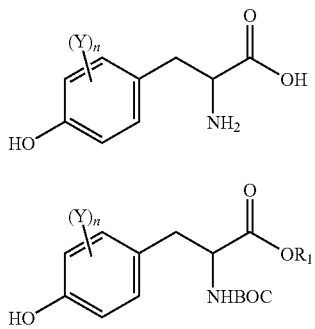

X

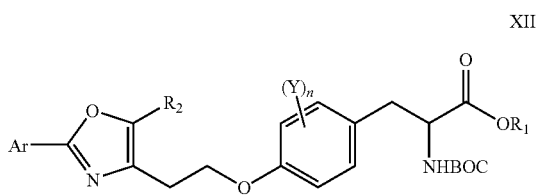

XI 3) reacting the compound of formula IX obtained in the step 1) with the compound of formula XI obtained in the step 2) to obtain a compound of formula XII;

XII

And deprotecting the compound of formula XII with trifluoroacetic acid to give the compound of formula III:

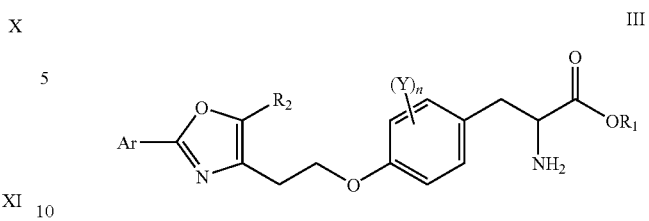

III wherein
- $R_1$ and $R_2$ are independently hydrogen, or $C_{1-4}$ straight or branched alkyl;
- Ar is phenyl ring which is unsubstituted or optionally substituted with 1 to 5 of the following groups: halogen, nitro, hydroxy, hydroxymethyl, trifluoromethyl, trifluoromethoxy, $C_1$-$C_6$ straight or branched alkyl, $C_2$-$C_6$ straight or branched alkenyl, $C_1$-$C_4$ alkoxy, $C_2$-$C_4$ alkenoxy, phenoxy, benzyloxy, carboxyl or amino;
- Y is hydrogen or halogen:
- n is an integer from 1 to 4; and
- $R_4$ represents $C_1$-$C_4$ alkyl.

8. A method for treating hyperglycemia, dyslipidemia, or type II diabetes mellitus including associated diabetic dyslipidemia comprising administering an effective amount of a compound according to claim 1.

9. A pharmaceutically acceptable dosage formulation form, for being administered orally, rectally, nasally, buccaly, topically, parenterally, or by inhalation spray, or via an implanted reservoir, comprising an effective amount of a compound according to claim 1.

* * * * *